United States Patent [19]

Thiel et al.

[11] Patent Number: 5,591,030
[45] Date of Patent: Jan. 7, 1997

[54] DENTAL CERAMIC RESTORATION USING A MULTI-LAYERED STRUCTURE

[75] Inventors: Norbert Thiel, Harpolingen; Susanne Weber, Schwörstadt, both of Germany

[73] Assignee: Vita Zahnfabrik H. Rauter GmbH & Co. KG, Bad Sackingen, Germany

[21] Appl. No.: 265,700

[22] Filed: Jun. 27, 1994

[30] Foreign Application Priority Data

Jun. 25, 1993 [DE] Germany .......................... 43 21 100.3
Sep. 21, 1993 [DE] Germany .......................... 43 32 025.2
Oct. 9, 1993 [DE] Germany .......................... 43 34 493.3

[51] Int. Cl.⁶ .................................................. A61C 13/08
[52] U.S. Cl. .................................... 433/212.1; 433/222.1; 433/223; 106/35
[58] Field of Search ............................ 433/212.1, 222.1, 433/223; 106/35

[56] References Cited

U.S. PATENT DOCUMENTS

| | | | |
|---|---|---|---|
| 4,358,271 | 11/1982 | Sperner et al. ......................... | 433/201 |
| 4,789,649 | 12/1988 | Abert et al. ............................ | 433/212.1 |
| 4,798,536 | 1/1989 | Katz ....................................... | 433/212.1 |
| 5,308,391 | 5/1994 | Komma et al. ....................... | 433/212.1 |
| 5,346,866 | 9/1994 | Komma et al. ....................... | 433/212.1 |

FOREIGN PATENT DOCUMENTS 2626092  12/1976  Germany .......................... 433/212.1

OTHER PUBLICATIONS

J. Falbe et al., Rompp Chemie Lexikon, 9. Aufl., pp. 132–135 (1989).

*Primary Examiner*—Edgar S. Burr
*Assistant Examiner*—Steven S. Kelley
*Attorney, Agent, or Firm*—Jacobson, Price, Holman & Stern, PLLC

[57] ABSTRACT

A dental ceramic restoration having a multi-layered structure on a core, obtainable by applying an opaque layer composed of from 50 to 60 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 0 to 6 wt.-% of $B_2O_3$, 5 to 12 wt.-% of $TiO_2$, and pigments, preferably on oxide basis, onto a core, followed by sintering this assembly, and thereafter applying dentin and enamel layers composed of from 50 to 60 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 2 to 10 wt.-% $B_2O_3$, preferably 4 to 8 wt.-% of $B_2O_3$, and pigments, preferably on oxide basis, onto a core, followed by firing this assembly.

13 Claims, No Drawings

DENTAL CERAMIC RESTORATION USING A MULTI-LAYERED STRUCTURE

This invention is directed to a dental ceramic restoration having a multi-layered structure on a core, and to the use of intermediate products for said dental ceramic restoration.

Dental ceramic restoration is a tightly fixed or removable denture which, for aesthetical and functional reasons is durably jacketed with tooth-colored ceramics. In order to obtain highest possible resemblance with natural teeth, ceramic layers which are fired subsequent to each operation, are applied to a metal framework. Hereby, a very good resemblance of the restoration to a natural tooth is achieved.

In general, the ceramic powders to be applied consist of various metal oxides, with the oxides of silicon generally constituting the major part.

According to current prior art, the following ceramic layers which are applied subsequent to the alloy are distinguished in the construction of the metal ceramics: Initially, a so-called opaque powder is coated onto the alloy. Using this powder, it can be achieved that the relatively dark metal framework of the metal ceramics does not appear translucent. Thereafter, dentin powder having a semi-transparency corresponding to natural dentin is layered first, then the relatively transparent enamel powder is layered and finally, various special effect powder may be used which enable individual adjustment to natural teeth. Between coating of each of the layers, various sintering procedures are carried out as required.

As the alloy, for example, metal alloys of gold and platinum are used which are silvery to light yellow. In order to obtain sufficient adherence between metal framework and the ceramic layers, the alloys are annealed at a temperature of about 950° C. prior to coating the ceramic powders. Here, by adding other elements an oxide layer is formed on the metal, permitting better adherence between metal and ceramics.

Meanwhile, in addition to these very costly alloys, there are alloys available on the market which have a golden yellow coloration and formerly were used as solid cast alloys for metallic and purely metallic denture. The proportion of copper in these alloys may be about from 3 to 7% but may also be considerably higher. Likewise, such alloys have to be oxide-annealed at a temperature of about 800° C. to improve adherence to the ceramic masses.

When using these alloys for metal ceramics, the problem arises that the ceramics subsequent to annealing undergo a black or green discoloration. Thus, for instance, black or green edges may be formed which are conspicuous and therefore, cannot be desirable for denture.

Similarly, ceramic powders familiar in the preparation of restorations according to prior art frequently do not meet the aesthetic demands because, in part, they tend to discoloration, or insufficient translucency or transparency of the dental ceramic restoration is observed. This results in an unnatural appearance of the denture. This is unsatisfactory in both medical and cosmetic view. Thus, the dental ceramic powders described in EP-0,475,528 or P 40 31 168 do not provide aesthetical results.

Therefore, the technical problem which the invention is based upon is to provide dental ceramic restorations avoiding the specified drawbacks of prior art.

This technical problem is solved by a dental ceramic restoration having a multi-layered structure on a core, obtainable by applying an opaque layer composed of from 50 to 60 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 0 to 6 wt.-% of $B_2O_3$, 5 to 12 wt.-% of $TiO_2$, and pigments, preferably on the oxide basis, onto a core, followed by firing this assembly, thereafter, applying dentin and enamel layers composed of from 50 to 60 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 2 to 10 wt.-% of $B_2O_3$, particularly 4 to 8 wt.-% of $B_2O_3$, and pigments, preferably on oxide basis, onto a core, followed by firing this assembly.

More specifically, the term dental ceramic restoration is understood to mean crowns, bridges, partial or full denture, etc., as well as partially ceramic restorations. The restoration either may have a metal or a full ceramic core.

In a preferred embodiment, a bonding layer (bonder) of the following composition of from 50 to 60 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 0 to 6 wt.-% of $B_2O_3$, 0 to 8 wt.-% of $TiO_2$, and optionally, 0 to 2 wt.-% of BaO is applied to the core as the first layer.

In particular, this bonder layer is advantageous where coupling between ceramic layer and metal core is necessary to effect better adherence. Subsequent to firing the bonder layer applied to the core, this assembly then is further processed using the opaque and dentin and enamel powders as described above.

By using a pre-opaque layer, particularly satisfactory results may be achieved in aesthetic terms. The pre-opaque comprises oxides selected from the group consisting of $SiO_2$, $Na_2O$, $K_2O$, $Al_2O_3$, and a reducing agent in form of a metal or non-metal selected from the group consisting of Sn, Al, Zn, Fe. Preferably, a pre-opaque layer between core and opaque layer and between bonder layer and opaque layer, respectively, is arranged. Here, each material prepared as described is provided with a pre-opaque powder of the following composition of from 45 to 55 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 0 to 6 wt.-% of $B_2O_3$, 0 to 6 wt.-% of $TiO_2$, and 2 to 20 wt.-% of $SnO_2$, and optionally 0 to 2 wt.-% of BaO, and subsequent to firing, is further processed as previously described.

In a particularly preferred embodiment, the pre-opaque has a metallic component which is a reducing agent. Particularly preferred are metals from the group of Sn, Al, Zn, Fe, which may be contained individually or in admixture.

Preferably, the reducing agents are contained in amounts of from 1 to 20 wt.-%, particularly preferred in amounts of from 1 to 15 wt.-%, and even more preferred in amounts of from 5 to 10 wt.-%, relative to the ceramic powder. The grain size of the reducing agent may be between from 1 to 50μ, with a range of from 1 to 35μ being preferred.

The respective ceramic powders, bonder, pre-opaque, opaque, and dentin and enamel masses, preferably in a modeling liquid, are applied to each assembly to be processed and then fired. Preferably, the modeling liquid used to premix the corresponding powders is based on aqueous systems.

The preparation of the dental metal ceramics system is effected in a per se known manner by mixing the solid single components and conventionally applying several powders layers onto the metal framework and subsequently, sintering these layers. Here, as previously described, the ceramic powders are applied to the metal framework in several layers. With metal frameworks containing copper, it has proven particularly useful to initially apply to the alloy a so-called bonder which improves bonding between metal and ceramic layer, and subsequently, to apply a pre-opaque layer containing the reducing agent in order to apply the further layers then, namely, opaque powder, dentin powder, enamel powder, and optionally, the special effect powder in the usual fashion and, subsequent to the application of each powders, to effect a firing procedure.

Such mode of operation has the advantage that alloys which so far have been used as solid cast alloys only, now may also be used for metal ceramics. Moreover, due to the higher proportion of copper, these alloys are substantially more economical than the former alloys of gold and platinum.

It was surprising that in spite of addition of reducing agent, which actually should result in removal of the oxide layer on the oxide-calcined alloy, sufficient bonding between metal component and ceramic component is retained. Thus, the achievement has been made to utilize alloys containing copper, which so far were deemed as non-jacketable solid cast alloys, in metal ceramics.

Preferably, the thermal expansion coefficients of each single layer range from 14.5 to $17.5 \times 10^6$ $k^{-1}$. The corresponding sintering temperatures of the powders employed, which build up the layers, are in the range of from 700° to 900° C.

As has been set forth, the core of a dental ceramic restoration may either consist of metal or may itself consist of ceramics. When using metal alloys as framework and core, respectively, it may be advantageous to apply the bonder layer first. In this case, it is recommendable to select the thermal expansion coefficients of the metal core and bonder layer materials such that the difference of the thermal expansion coefficients is in the range of from 0.5 to 1.5 units, with the alloy having the higher thermal expansion coefficient. Additional ceramic layers to be applied subsequently then may be subject to a further gradation towards lower thermal expansion coefficients.

Similarly, when using ceramic frameworks or cores, it is advantageous to select the difference of the thermal expansion coefficients in the range of from 0.5 to 1.5 units between framework or core and the first layer arranged thereon. Depending on the nature of the ceramic core, the application of a bonder layer may also be abandoned.

The present invention also relates to the intermediate products specified in claims 8 to 12 both as final admixture in solid, powdery form or premixed with appropriate modeling liquids.

The specified components are suitable to be employed in the preparation of dental ceramic restorations according to the invention.

The invention will be discussed in more detail in the following Example.

EXAMPLE

Initially, a framework for dental ceramic restoration (metallic core) is worked out in known manner. Subsequently, the bonder powder composed of 57.13 wt.-% of $SiO_2$, 6.63 wt.-% of $Na_2O$, 1.47 wt.-% of CaO, 11.47 wt.-% of $K_2O$, 15.7 wt.-% of $Al_2O_3$, 3.06 wt.-% of $B_2O_3$, and 3.7 wt.-% of $TiO_2$, is premixed with modeling liquid and applied.

Then, the assembly is calcined under vacuum at 800° C. Subsequently, the pre-opaque layer is applied. As the pre-opaque, the following mixture is used: 51.8 wt.-% of $SiO_2$, 5.96 wt.-% of $Na_2O$, 1.27 wt.-% of CaO, 10.02 wt.-% of $K_2O$, 14.4 wt.-% of $Al_2O_3$, 2.796 wt.-% of $B_2O_3$, 3.09 wt.-% of $TiO_2$, and 10.63 wt.-% of $SnO_2$.

Subsequent to application of the pre-opaquer layer, the assembly is likewise sintered under vacuum at 800° C. for about 2 minutes.

Thereafter, the opaque composed of 54.8 wt.-% of $SiO_2$, 7.1 wt.-% of $Na_2O$, 1.4 wt.-% of CaO, 10.6 wt.-% of $K_2O$, 15.0 wt.-% of $Al_2O_3$, 2.3 wt.-% of $B_2O_3$, and 8.8 wt.-% of $TiO_2$, is premixed with modeling liquid and applied and fired at about 800° C. Thereon, the dentin and enamel powders of the following composition of 57.5 wt.-% of $SiO_2$, 6.7 wt.-% of $Na_2O$, 1.8 wt.-% of CaO, 11.2 wt.-% of $K_2O$, 17.1 wt.-% of $Al_2O_3$, and 5.7 wt.-% of $B_2O_3$ are applied and fired at about 800° C. This may be followed by a glaze firing using common painting colors such as Vitachrom "L" and Vitachrom Delta Stains painting colors. This firing likewise is conducted at about 800° C.

What is claimed is:

1. A dental ceramic restoration having multiple layers disposed on a core obtained by:

a) applying to the core a ceramic opaque layer comprised of 50 to 60 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 0 to 6 wt.-% of $B_2O_3$, 5 to 12 wt.-% of $TiO_2$, and pigments, effecting a first assembly;

b) sintering the first assembly;

c) applying to the sintered first assembly a ceramic dentin-and-enamel layer comprised of 50 to 60 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 2 to 10 wt.-% of $B_2O_3$, and pigments, to obtain a second assembly; and d) sintering the second assembly.

2. The dental ceramic restoration according to claim 1 wherein:

i) before applying the opaque layer, applying to the core a ceramic bonding layer, comprised of 50 to 60 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 0 to 6 wt.-% of $B_2O_3$, 0 to 8 wt.-% of $TiO_2$, and, 0 to 2 wt.-% of BaO, is applied to the core and sintered; and ii) the opaque layer is, then, applied to the sintered bonding layer.

3. The dental ceramic restoration according to claim 2 wherein:

i) prior to applying the opaque layer, a ceramic pre-opaque layer, comprised of 45 to 55 wt.-% of $SiO_2$, 4 to 10 wt.-% of $Na_2O$, 0 to 2.5 wt.-% of CaO, 8 to wt.-% of $K_2O$, 10 to 20 wt.-% of $Al_2O_3$, 0 to 6 wt.-% of $B_2O_3$, 0 to 6 wt.-% of $TiO_2$, 2 to 20 wt.-% of $SnO_2$, and 0 to 2 wt.-% of BaO, is applied to the sintered bonding layer and sintered; and ii) the opaque layer is, then, applied to the sintered pre-opaque layer.

4. The dental ceramic restoration according to claim 1 wherein:

i) prior to applying the opaque layer, a pre-opaque layer, comprised of 45 to 55 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 0 to 6 wt.-% of $B_2O_3$, 0 to 6 wt.-% of $TiO_2$, 2 to 20 wt-% of $SnO_2$, and, 0 to 2 wt.-% of BaO, is applied to the core and sintered; and ii) the opaque layer is, then, applied to the sintered pre-opaque layer.

5. The dental ceramic restoration according to claim 1, wherein the thermal expansion coefficient of each ceramic layer is in the range of 14.5 to $17.5 \times 10^{-6} k^{-1}$, and the sintering temperature of each ceramic layer is in the range of 700° to 900° C.

6. The dental ceramic restoration according to claim 1, wherein the core is selected from the group consisting of a metallic core and a ceramic core.

7. The dental ceramic restoration according to claim 6 wherein the thermal expansion coefficient of the core is higher by 0.5 to 1.5 units than that of the layer adjacent to the core.

8. The dental ceramic restoration according to claim 6, wherein the core is a metal alloy having a solidus temperature of at least 50° C. above the sintering temperature of the ceramic layers.

9. The dental ceramic restoration according to claim 6, wherein the core is a metallic core.

10. The dental ceramic restoration according to claim 6, wherein the core is a ceramic core.

11. A method comprising combining a bonder and the dental ceramic restoration of claim 1, comprising the steps of:

a) applying to the core a ceramic opaque layer comprised of 50 to 60 wt.-% of $SiO_2$, 4 to 10 wt.-% of $Na_2O$, 0 to 2.5 wt.-% Of CaO, 8 to 14 wt.-% of $K_2O$, 10 to 20 wt.-% of $Al_2O_3$, 0 to 6 wt.-% of $B_2O_3$, 5 to 12 wt.-% of $TiO_2$, and pigments, effecting a first assembly;

b) sintering the first assembly;

c) applying to the sintered first assembly a ceramic dentin-and-enamel layer comprised of 50 to 60 wt.-% of $SiO_2$, 4 to 10 wt.-% of $Na_2O$, 0 to 2.5 wt.-% of CaO, 8 to 14 wt.-% of $K_2O$, 10 to 20 wt.-% of $Al_2O_3$, 2 to 10 wt.-% of $B_2O_3$, and pigments, to obtain a second assembly; and d) sintering the second assembly; wherein:
   i) before applying the opaque layer, the bonder is applied to the core as a bonding layer and sintered; and
   ii) the opaque layer is, then, applied to the sintered bonding layer.

12. The restoration of claim 1 wherein the $B_2O_3$ in the dentin and enamel layer is present in an amount of 4 to 8 wt.-%.

13. The method of claim 11 wherein the $B_2O_3$ in the dentin-and-enamel layer is present in an amount of 4 to 8 wt.-%.

* * * * *